(12) United States Patent
Albrektsson et al.

(10) Patent No.: US 7,156,879 B1
(45) Date of Patent: ***Jan. 2, 2007

(54) FEMUR FIXTURE AND SET OF FEMUR FIXTURES

(75) Inventors: Tomas Albrektsson, Mölndal (SE); Lars Carlsson, Kullavik (SE); Magnus Jacobsson, Göteborg (SE); Warren MacDonald, Bournemouth (GB); Stig Wennberg, Gunnilse (SE)

(73) Assignee: Astra Tech AB, Molndal (SE)

( * ) Notice: Subject to any disclaimer, the term of this patent is extended or adjusted under 35 U.S.C. 154(b) by 112 days.

This patent is subject to a terminal disclaimer.

(21) Appl. No.: 10/089,848

(22) PCT Filed: Oct. 6, 2000

(86) PCT No.: PCT/SE00/01945

§ 371 (c)(1),
(2), (4) Date: Jun. 25, 2002

(87) PCT Pub. No.: WO01/24738

PCT Pub. Date: Apr. 12, 2001

(30) Foreign Application Priority Data

Oct. 6, 1999 (SE) .................................. 9903607
Oct. 6, 1999 (SE) .................................. 9903612

(51) Int. Cl.
*A61F 2/36* (2006.01)

(52) U.S. Cl. .............................. 623/23.14; 623/23.27; 606/65

(58) Field of Classification Search ............. 623/23.11, 623/23.12, 23.14, 23.15, 23.18, 23.21–23.29, 623/23.31, 23.35, 23.44; 606/65, 73; 433/174
See application file for complete search history.

(56) References Cited

U.S. PATENT DOCUMENTS 2,570,465 A * 10/1951 Lundholm ................... 606/65

(Continued)

FOREIGN PATENT DOCUMENTS

DE 3607824 A1 * 9/1987

(Continued)

*Primary Examiner*—Corrine McDermott
*Assistant Examiner*—Javier G. Blanco
(74) *Attorney, Agent, or Firm*—Birch, Stewart, Kolasch & Birch, LLP

(57) ABSTRACT

A femur fixture for a hip-joint prosthesis comprising an intraosseous anchoring structure of a generally circular cross-section for screwing laterally into a complementary bore drilled laterally into the neck of a femur after resection of the femur head to an anchored position. The intraosseous anchoring structure has a proximal end, a distal end, a relatively short frusto-conical proximal section at the proximal end, and a proximal cylindrical section having a screw thread profile thereon. The proximal cylindrical section extends from the frusto-conical proximal section towards the distal end of the anchoring structure. The frusto-conical proximal section and the proximal cylindrical section each being dimensioned so as to bear against the cortex of the femur neck when the intraosseous anchoring structure is in the anchored position. The invention also relates to a set of such femur fixtures, wherein the frusto-conical proximal section and the proximal cylindrical section of each fixture in the set have different dimensions, whereby the fixture in the set having the frusto-conical proximal section and the proximal cylindrical section of correct size for abutting the cortex of the femur neck of a particular patient can be selected for use in that patient.

37 Claims, 9 Drawing Sheets

U.S. PATENT DOCUMENTS

| | | | |
|---|---|---|---|
| 3,051,169 A * | 8/1962 | Grath | 606/65 |
| 3,996,625 A | 12/1976 | Noiles | |
| 4,051,559 A | 10/1977 | Pifferi | |
| 4,129,903 A * | 12/1978 | Huggler | 623/23.11 |
| 4,224,699 A * | 9/1980 | Weber | 623/23.14 |
| 4,976,740 A * | 12/1990 | Kleiner | 623/23.14 |
| 5,098,434 A * | 3/1992 | Serbousek | 606/73 |
| 5,310,343 A * | 5/1994 | Hasegawa et al. | 433/173 |
| 5,360,448 A * | 11/1994 | Thramann | 606/60 |
| 5,588,838 A * | 12/1996 | Hansson et al. | 433/173 |
| 5,593,410 A * | 1/1997 | Vrespa | 606/73 |
| 5,639,237 A * | 6/1997 | Fontenot | 433/173 |
| 5,766,263 A * | 6/1998 | Grundei et al. | 623/23.15 |
| 5,863,167 A * | 1/1999 | Kaneko | 411/426 |
| 5,961,329 A * | 10/1999 | Stucki-McCormick | 433/173 |
| 6,284,002 B1 * | 9/2001 | Sotereanos | 623/27 |
| 6,364,664 B1 * | 4/2002 | Watanabe | 433/174 |
| 6,383,227 B1 * | 5/2002 | Baroud et al. | 623/23.22 |
| 6,585,740 B1 * | 7/2003 | Schlapfer et al. | 606/73 |
| 6,626,948 B1 * | 9/2003 | Storer et al. | 623/23.14 |
| 6,695,883 B1 * | 2/2004 | Crofford | 623/22.46 |

FOREIGN PATENT DOCUMENTS

| | | | |
|---|---|---|---|
| DE | 19725269 A1 * | 1/1999 | |
| EP | 0 567 349 A1 | 10/1993 | |
| FR | 2674122 A1 * | 9/1992 | |
| GB | 2033755 A * | 5/1980 | |
| JP | 11056883 A * | 3/1999 | |
| WO | WO 9316663 A1 * | 9/1993 | |
| WO | 97/25939 A1 | 7/1997 | |

* cited by examiner

FEMUR FIXTURE AND SET OF FEMUR FIXTURES

This application is the national phase under 35 U.S.C. § 371 of PCT International Application No. PCT/SE00/01945 which has an International filing date of Oct. 6, 2000, which designated the United States of America.

FIELD OF THE INVENTION

The present invention relates to a femur fixture for a hip-joint prosthesis comprising an intraosseous anchoring structure of a generally circular cross-section adapted for screwing laterally into a complementary bore drilled laterally into the neck of a femur after resection of the femur head to an anchored position. The invention also relates to a set of such femur fixtures.

BACKGROUND OF THE INVENTION

A femur fixture of the aforementioned type is disclosed in Applicant's prior International patent application publication WO93/16663. In this femur fixture the intraosseous structure has a screw threaded cylindrical section at the proximal end. The use of a cylindrical proximal section in the intraosseous structure of the femur fixture of WO93/16663 enables the threads thereon to engage with the cortex of the femur neck and increase the fixation strength of the femur fixture in the femur. However, the threads at the terminal proximal section of the cylindrical section do not register in the medial cortex of the femur neck at the resected surface. This is due to the cortex of the femur neck flaring outwardly adjacent the resected surface.

This lack of loading of the cortex at the resected surface of the femur by the intraosseous anchoring structure of the femur fixture can lead to bone resorption at the resected surface. This situation is not able to be simply addressed by increasing the diameter of the cylindrical proximal section of the intraosseous anchoring structure of the WO93/16663 femur fixture since it would result in the threads of the cylindrical proximal section puncturing the cortex in the body of the femur neck or being dangerously close to puncturing the cortex due to the trumpet-like shape of the cortex in the femur neck.

SUMMARY OF THE INVENTION

Thus, the object of the present invention is to provide an improved femur fixture where the above mentioned drawback is addressed.

This and other objects are achieved according to the present invention by providing a femur fixture having the features defined in the independent claim. Preferred embodiments are defined in the dependent claims.

According to the present invention there is provided a femur fixture for a hip-joint prosthesis, comprising an intraosseous anchoring structure of a generally circular cross-section for screwing laterally into a complementary bore drilled laterally into the neck of a femur after resection of the femur head to an anchored position. The intraosseous anchoring structure has a proximal end, a distal end, a relatively short frusto-conical proximal section at the proximal end, and a proximal cylindrical section having a screw thread profile thereon and extending towards the distal end from the frusto-conical proximal section, the frusto-conical proximal section and the proximal cylindrical section each being dimensioned so as to bear against the cortex of the femur neck when the intraosseous anchoring structure is in the anchored position.

Thus, the present invention is based on the advantageous idea of providing a femur fixture of the above-mentioned type with a relatively short frusto-conical proximal section at the proximal end of the intraosseous anchoring structure.

The provision of a relatively short frusto-conical proximal section at the proximal end of the intraosseous anchoring structure thus loads the cortex of the femur neck adjacent the resected surface and the proximal cylindrical section loads the cortex in the body of the femur neck. Thereby, an improved anchorage of the femur fixture in the femur of the patient can be obtained.

The frusto-conical section preferably has a flank angle in the range of 8–15°, preferably in the range 10–13°, even more preferably approximately 12°.

According to preferred embodiments of the invention the frusto-conical section has an axial extent in the range of 5–10 mm. Preferably, the axial extent is approximately 8 mm.

Advantageously, the proximal end of the frusto-conical proximal section has a diameter in the range of 18–30 mm.

Advantageously, the distal end of the frusto-conical proximal section, i.e. the end interfacing the proximal cylindrical section, has essentially the same diameter as the proximal cylindrical section. Thus, there will be no sharp edges in the transition area between the frusto-conical proximal section and the proximal cylindrical section that could induce undesired stresses.

According to preferred embodiments of the invention the frusto-conical section has at least partly a roughened surface. This improves the integration of the frusto-conical section with the cortex (termed "osseointegration" in the art). The roughening may be achieved by grit blasting, etching or machining, or by a combination of one or more of these roughening techniques.

Alternatively or additionally, the frusto-conical proximal section could be provided with a circumferentially oriented roughness, preferably machined. Such circumferentially oriented roughness could for instance be provided in the form of grooves, beads, tracks, or screw threads. The provision of such a circumferentially oriented roughness would improve the short term anchorage capacity of the intraosseous anchoring structure due to the engagement of the circumferentially oriented roughness with the cortex of the femur neck adjacent the resected surface, as well as even further promote the osseointegration process.

According to an embodiment of the invention, the frusto-conical proximal section is provided with a screw thread profile similar to that of the proximal cylindrical section.

According to preferred embodiments of the invention, the frusto-conical proximal section has a screw thread profile of a height less than the screw thread profile of the proximal cylindrical section. Preferably, the height of the screw thread profile on the frusto-conical proximal section is no greater than 0.3 mm (microthreads), more preferably in the range 0.1–0.25 mm, and even more preferably approximately 0.2 mm.

According to another embodiment of the invention, the frusto-conical proximal section is provided with circumferential beads of a height less than the screw thread profile of the proximal cylindrical section. Preferably, the height of the beads is no greater than 0.3 mm, more preferably in the range 0.1–0.25 mm, and even more preferably approximately 0.2 mm.

According to preferred embodiments of the invention, the intraosseous anchoring structure is dimensioned such that that the distal end of the anchoring structure projects through the lateral cortex of the femur when the intraosseous anchoring structure is in the anchored position. This arrangement, together with the inventive features of having a frusto-conical proximal section at the proximal end of the anchoring structure, provides a strong anchorage of the anchoring structure in the cortical bone tissue of the femur.

Advantageously, the intraosseous anchoring structure further has a screw threaded, distal cylindrical section, which extends from the distal end of the intraosseous anchoring structure towards the proximal cylindrical section. The diameter of the distal cylindrical section is less than the diameter of said proximal cylindrical section. Preferably, the screw thread profiles of the proximal and distal cylindrical sections are essentially the same.

According to an embodiment of the invention, the intraosseous anchoring structure further comprises a tapered connecting section provided between the proximal and distal cylindrical sections. This tapered connecting section interconnects the proximal and distal cylindrical sections and, preferably, has a frusto-conical shape which at one end has a base diameter essentially equal to the diameter of said proximal cylindrical section, and at the other end has a top diameter essentially equal to the diameter of said distal cylindrical section.

The provision of a tapered connecting section would radically reduce any stresses that might be induced by a sharp, step-wise transition between the cylindrical sections of differing diameters. Further, insertion of the fixture would be facilitated, the short and long term stability of the fixture would be improved, as well as the process of osseointegration between the fixture and the surrounding bone tissue.

Advantageously, the proximal end of the tapered connecting section has essentially the same diameter as the proximal cylindrical section. Likewise, the distal end of the tapered connecting section advantageously has essentially the same diameter as the distal cylindrical section.

According to preferred embodiments of the invention, the diameter of the first cylindrical section is adapted to the actual size and shape of the femur of the particular patient for whom the femur fixture is intended. Thus, the diameter of the first cylindrical section can vary considerably. However, the diameter of the second cylindrical section is preferably dimensioned to be within a short, limited range. Thus, the flank angle of the connecting section may vary in dependence of the actual dimensions of the first and second cylindrical sections. Preferably, the flank angle can be varied in the range of 10°–50°, and more preferably in the range of 20°–40°. Preferably, the tapered connecting section is at least partly provided with a roughened surface. This would even further promote the osseointegration process at the transition area between the cylindrical sections. The roughened surface could be achieved through blasting, preferably grit-blasting, etching, or the like. Alternatively or additionally, the surface of the tapered proximal section is provided with a circumferentially oriented roughness, for instance in the form of circumferential beads or screw threads. The height of the beads or screw threads is preferably no greater than 0.3 mm, more preferably in the range of 0.1–0.25 mm, and even more preferably approximately 0.2 mm.

According to an embodiment of the invention as hereinafter described, the tapered connecting section is at least in part provided with one or more self-tapping cutting recesses.

According to preferred embodiments of the present invention, femur fixture further comprises a head section. The head section is provided with a collar abutting the tapered proximal section, which collar delimits the insertion of the femur fixture into bone tissue. Preferably, the surface of the collar facing the proximal section is inclined inwardly so as to mate with a resected bone tissue surface that has been given a correspondingly inclined shape. Preferably, the angle of inclination is within the range of 10°–20°, preferably approximately 15°. Alternatively, the surface of the collar facing the proximal section is given a concave shape, so as to mate with a convex bone tissue surface. Thereby, an improved contact between the femur fixture and the bone surface can be obtained.

Preferably, said collar surface is provided with radially spaced circular beads or grooves for increasing the stability of the inserted femur fixture and promote the osseointegration between the femur fixture and the bone tissue. Preferably, these beads have a height in the range of 0.1–0.5 mm, preferably in the range of 0.2–0.4 mm, and even more preferably approximately 0.3 mm.

According to a preferred embodiment the present invention there is further provided a set of femur fixtures according to the invention with the frusto-conical proximal section and the proximal cylindrical section of each fixture in the set having different dimensions, whereby the fixture in the set having the frusto-conical and cylindrical sections of correct size for abutting the cortex of the femur neck of a patient can be selected for use in that patient.

According to a preferred embodiment of the invention, there is further provided a set where the frusto-conical proximal section and the proximal cylindrical section of each fixture in the set have different dimensions, while the dimension of the distal cylindrical section is essentially the same for all fixtures in the set. Thereby, the fixture in the set having the frusto-conical and cylindrical sections of correct size for abutting the cortex of the femur neck of a particular patient can be selected for use in that patient.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF EXEMPLARY EMBODIMENT

Figure 1:
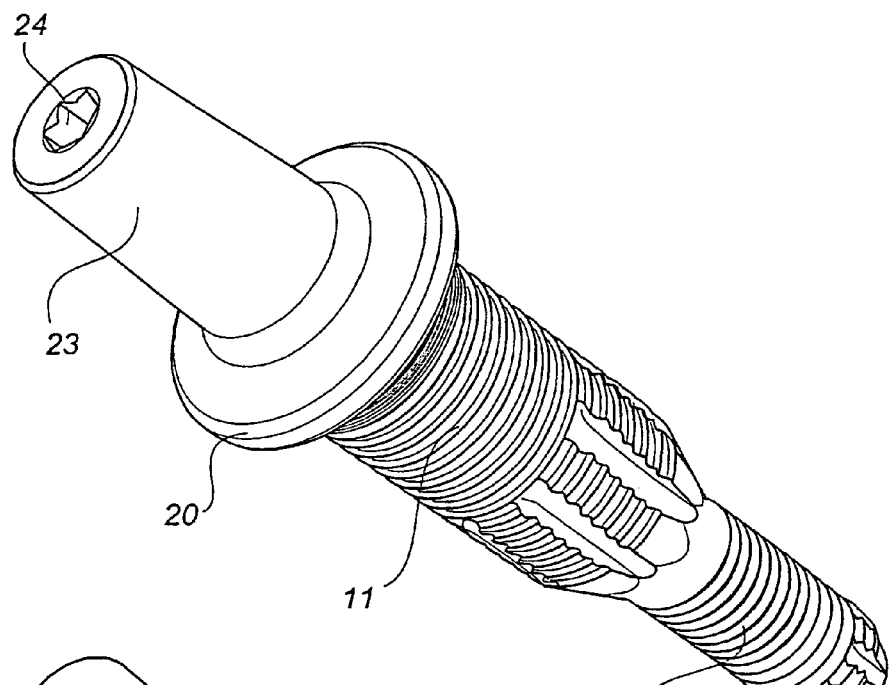
FIG. 1 is a perspective view of a femur fixture for a hip-joint prosthesis in accordance with an embodiment of the invention.

With reference to FIGS. 1–8, there is shown an integrally formed femur fixture 1 for a hip-joint prosthesis preferably made from commercially pure titanium and consisting of (i) an intraosseous anchoring section 3 of circular cross-section, and (ii) a head section 5. The anchoring section 3 is intended for insertion laterally into a cavity 30 of complementary profile (FIG. 7), said cavity 30 being drilled into the neck of a femur through a resected section 33 made by resection of the head of the femur. The head section 5 of the fixture, which will protrude from the resected section 33 when the intraosseous anchoring section 3 is located in the cavity 30 (FIG. 8), is arranged for supporting a ball 25 of the hip-joint prosthesis which interacts with the anatomical acetabular cavity or an acetabular part of the hip-joint prosthesis where a total hip-joint prosthesis is required.

Figure 2:
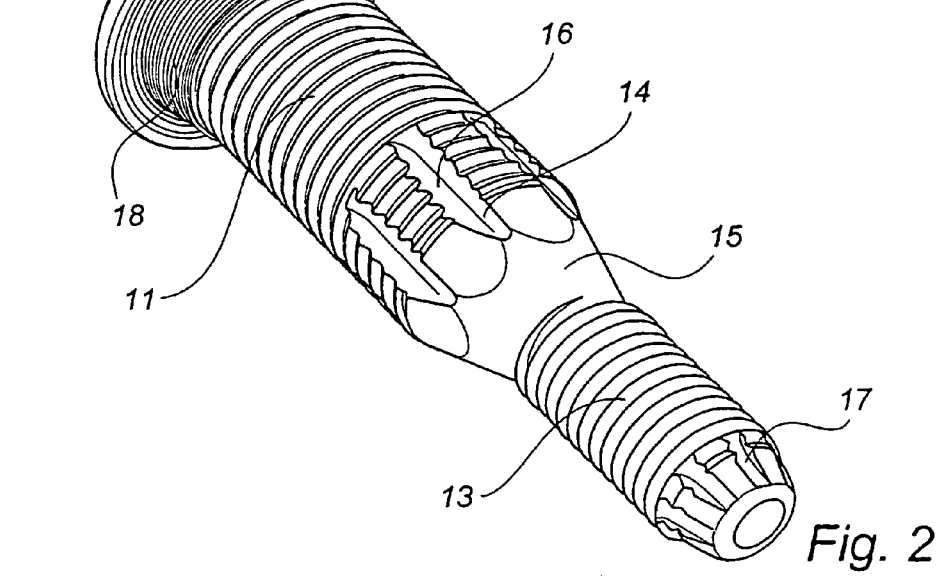
FIG. 2 is an opposite perspective view of the femur fixture shown in FIG. 1.
Figures 3, 4:
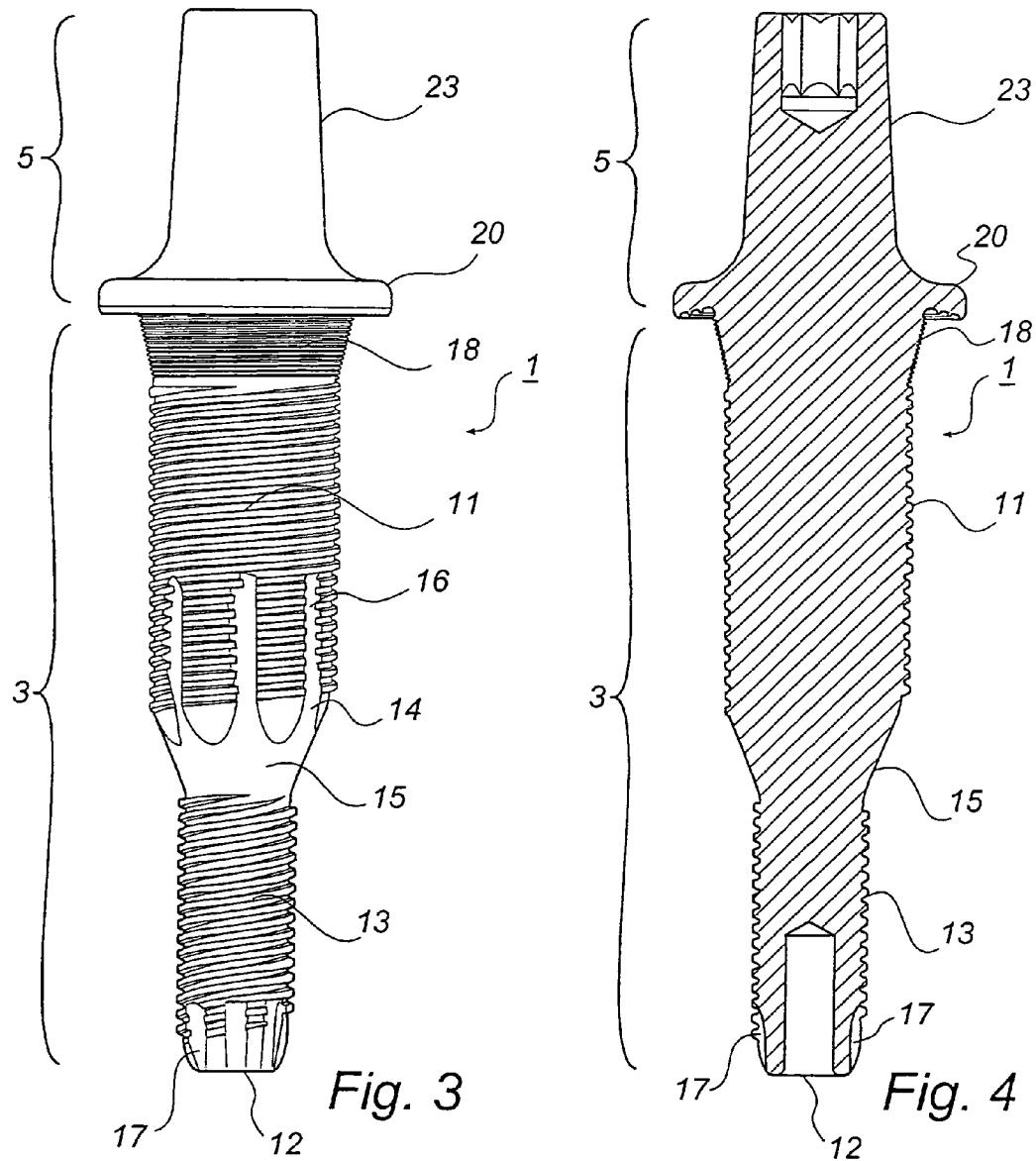
FIG. 3 is a longitudinal side view of the femur fixture.
FIG. 4 is a longitudinal sectional view of the femur fixture.

As can be seen in FIGS. 1–3, the intraosseous anchoring section 3 has proximal and distal cylindrical sections 11, 13 of different outer diameter, with the diameter of the proximal cylindrical section 11 being greater than that of the distal cylindrical section 13. The intraosseous anchoring section 3 further has a tapered terminal distal section 12, contiguous with the distal cylindrical section 13, a frusto-conical connecting section 15 connecting the proximal cylindrical section 11 to the distal cylindrical section 13, and a frusto-conical proximal section 18 connecting the proximal cylindrical section 11 to the head section 5.

The proximal cylindrical section 11 presents a screw-threaded outer surface for screwing into an outer bone cavity section 32 of said cavity. The distal cylindrical section 13 also presents a screw-threaded outer surface, for screwing into a narrow drilled hole 31, which is coaxial with said outer cavity section 32. The screw-threads of the proximal cylindrical section 11 have the same pitch and height as those of the distal cylindrical section 13.

Figure 7:
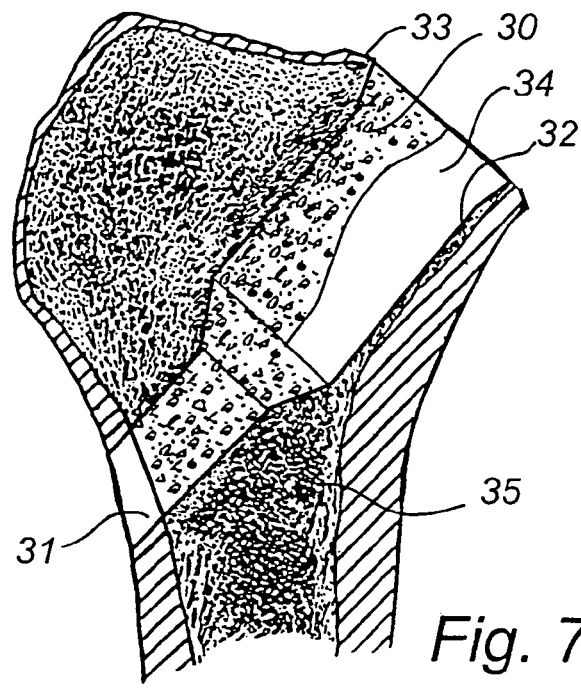
FIG. 7 is a fragmentary sectional view of the collum of the human femur; with a cavity formed therein for reception of the femur fixture.

The major diameters of the screw threads on the proximal and distal cylindrical sections 11, 13 are sized to be greater than the inner diameter of complementary cylindrical sections of the outer cavity section 32 and the drilled hole 31 provided in the cavity 30 of the femur neck (See FIG. 7). Accordingly, the intraosseous anchoring section 3 is able to be anchored in the cavity 30 by screwing of the femur fixture 1 into the cavity 30, with the screw threads on the proximal and distal cylindrical sections 11, 13 threading into the bone tissue in the boundary wall of the cavity 30.

Figure 8:
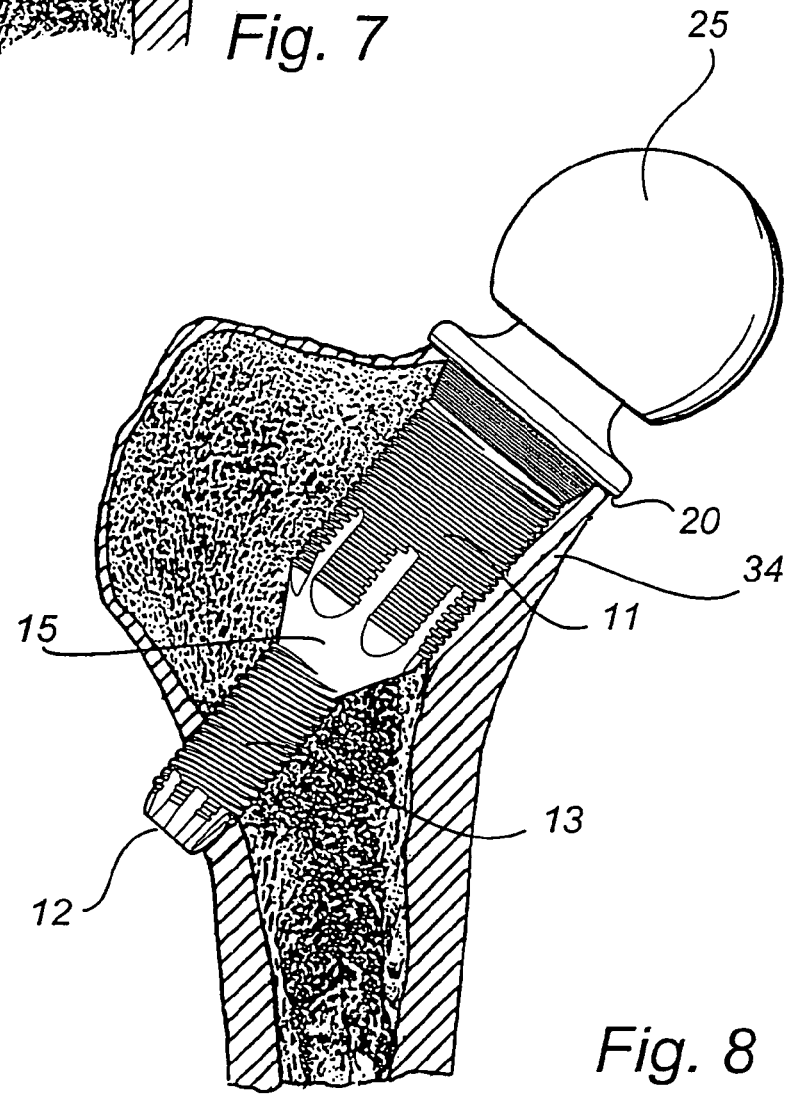
FIG. 8 is a fragmentary sectional view of the collum of the human femur, with the femur fixture inserted therein.

As seen in FIG. 8, the diameter of the proximal cylindrical section 11 is in fact sized such that the threads thereon register in the peripheral layer of cortical bone 34 in the femur neck, as outlined in WO93/16663 and WO97/25939. The threads on the proximal cylindrical section 11 are thus secured in the stronger cortical bone 34 as opposed to the spongier cancellous bone 35, thereby giving the femur fixture 1 greater fixation in the femur neck. Due to the fact that the femur dimensions can vary from patient to patient, the diameter of the proximal cylindrical section can vary in the range from approximately 16–26 mm (cf. FIGS. 3 and 8).

As illustrated in FIG. 8, the axial length of the intraosseous anchoring section 3 is such that in the anchored position of the intraosseous anchoring section 3, the distal end 12 thereof projects through the lateral cortex 34 of the femur.

Figure 5:
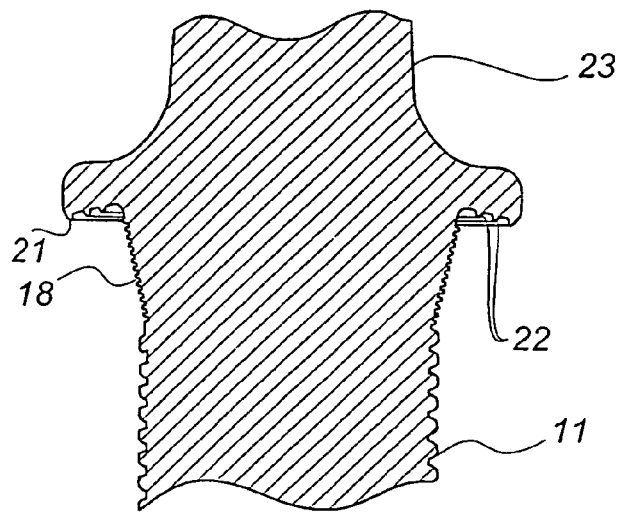
FIG. 5 is an enlarged fragmentary sectional view showing the tapered proximal section and the head of the femur fixture.

With reference to FIGS. 3–5, the frusto-conical proximal section 18 also has threads thereon. The height of these threads is 0.2 mm (so-called microthreads) which is less than that of the threads on the proximal and distal cylindrical sections 11, 13. Further, the frusto-conical proximal section 18 is sized so that the microthreads engage with the cortex 34 of the femur neck at the resected surface. In the embodiment described herein, the frusto-conical terminal proximal section 18 has a flank angle of approximately 12°, and an axial extent of approximately 8 mm.

The distal diameter of the proximal section 18 is adapted to the diameter of the neighbouring proximal cylindrical section 11, such that there are no sharp edges in the transition area between the frusto-conical proximal section 18 and the proximal cylindrical section 11. Consequently, the proximal diameter of the frusto-conical proximal section 18 is in the range of approximately 20–30 mm.

The diameter of the distal cylindrical section 13 does not have to be varied in dependence of the femur dimensions of the patient. The diameter of the distal cylindrical section 13 is approximately 11 mm, or within the range of 10–12 mm.

The frusto-conical connecting section 15 interconnects the proximal and distal cylindrical sections 11, 13 to one another. In this embodiment, the diameters at the respective end of the connecting section 15 correspond to the diameters of the proximal and distal cylindrical sections 11, 13, respectively. In other words, the distal end of the connecting section 15 has essentially the same diameter as the distal cylindrical section 13, and the proximal end of the connecting section 15 has essentially the same diameter as the proximal cylindrical section 11.

As a result of the fact that the diameter of the proximal cylindrical section 11 can be varied between different femur fixtures, while the diameter of the distal cylindrical section 13 is not varied, the dimensions of the connecting section will be varied in accordance with the varying difference in diameter between the proximal cylindrical section 11 and the distal cylindrical section 13. Since the axial extent of the connecting section is kept relatively short, i.e. within the range of approximately 7.5–10.5 mm, the flank angle of the connecting section can vary from approximately 20° for the narrowest fixture alternative, up to approximately 37° for the widest fixture alternative.

In the herein described embodiment of the invention, the surface of the frusto-conical connecting section 15 is provided with a grit-blasted surface for promoting the osseointegration between the surface and the surrounding cancellous bone tissue. The surface could also, or alternatively, be provided with a screw thread profile for promoting said osseointegration and improve the anchorage of the femur fixture 1. As a further alternative, the frusto-conical connecting section 15 may be left smooth, even polished.

As can be seen in FIGS. 2 and 3, bridging the boundary between the proximal cylindrical section 11 and the frusto-conical connecting section 15 are a series of equi-spaced, circumferentially-arranged, sharp-edged cutting recesses or notches 14 for self-tapping into a pre-cut outer bone cavity section 32. The cutting recesses 14 each communicate with a channel 16 in the proximal cylindrical section 11 for autologous transplantation of the bone cut by the cutting recesses 14 as the femur fixture 1 is screwed into the bore in the femur neck, as detailed in WO97/25939.

Further, bridging the boundary between the distal cylindrical section 13 and the tapered terminal distal section 12 are also a series of short, sharp-edged circumferentially-arranged cutting recesses 17 for the distal cylindrical section 13 to be self-tapped into said drilled, relatively narrow hole 31.

Figure 6:
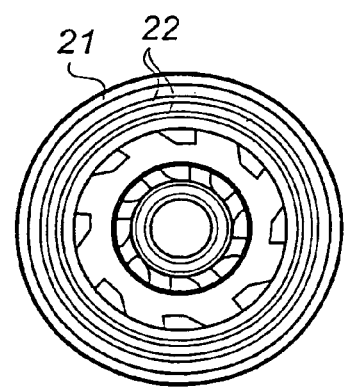
FIG. 6 is a bottom view of the femur fixture.

With reference to FIGS. 1, 7 and 8, the head section 5 of the femur fixture 1 has a collar section 20 and a tapered mounting section 23 for the ball component 25 of the hip-joint prosthesis to be mounted on. The mounting section 23 is provided with a recess 24 for reception of the ball component 25. The collar section 20 delimits the insertion of the intraosseous anchoring section 3 into the bore in the femur neck by abutting with the resected femur section 33 adjacent the opening to the cavity 30. As can be seen in FIG. 5, the distal surface 21 (FIG. 5) is inclined inwardly for mating with a correspondingly inclined bone surface of the resected femur section 33 (FIG. 7). The angle of inclination in the embodiment herein described is approximately 15'. Further, as seen in FIG. 6, for improved anchorage and osseointegration, the distal surface 21 of the collar section 20 is provided with radially spaced, circumferential beads 22, said beads having a height of approximately 0.3 mm.

The surgical procedures described in WO93/16663 and WO97/25939 for implanting the femur fixtures disclosed therein can also be adapted for implantation of the femur fixture 1 and as such are incorporated herein by reference.

The anchorage of the femur fixture 1 is primarily reliant on the registration of the threads in the bone of the femur, principally the registration of the threads on the proximal cylindrical section 11 in the cortex 34 of the femur neck and the registration of the threads on the distal cylindrical section 13 in the lateral cortex 34 of the femur. This is in distinction to femur fixtures which rely on a thrust plate mechanism for their fixation, for example as in GB-A-2033755.

The femur fixture 1 herein described with reference to the accompanying figures can be varied in numerous ways within the scope of the invention. For instance, the femur fixture 1 could be in the form of an assembly in which the component parts are assembled (i) for insertion thereof laterally into the bore as a one-piece structure, as disclosed in WO93/16663, or (ii) by connecting the parts together in the bore, as disclosed in WO93/01769. The femur fixture 1 could also be made from any biocompatible material of strength sufficient to withstand the loads imposed upon it in situ.

Figure 9:
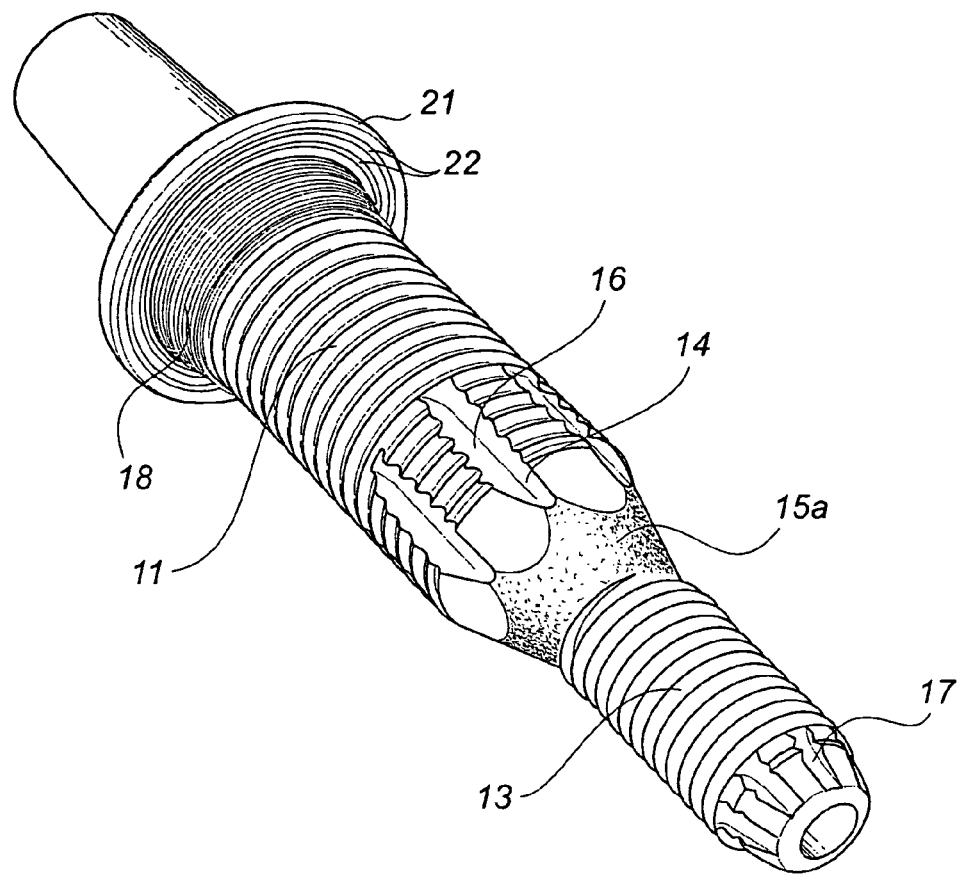
FIG. 9 is a perspective view similar to FIG. 2 of the femur fixture with a roughened surface which is at least partially blasted.
Figure 10:
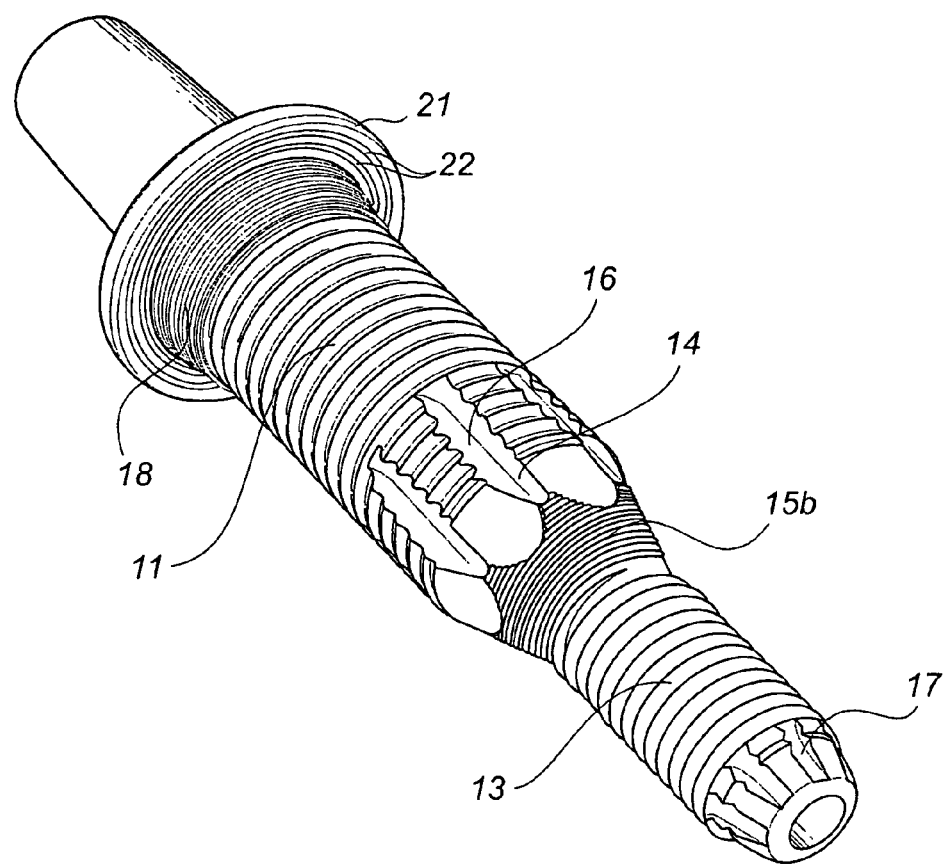
FIG. 10 is a perspective view similar to FIG. 9 of the femur fixture with a connecting section having circumferential beads.

Turning now to FIG. 9 an embodiment of the femur fixture is shown with a connecting section 15a having a roughened surface which is at least partly a blasted surface. In FIG. 10, a connecting section 15b is shown having a roughened surface 15 which is at least partly provided with a circumferentially oriented roughness in the form of circumferential beads that have a height less than that of the screw thread profiles of the first and second cylindrical sections and no greater than 0.3 mm.

Figure 11:
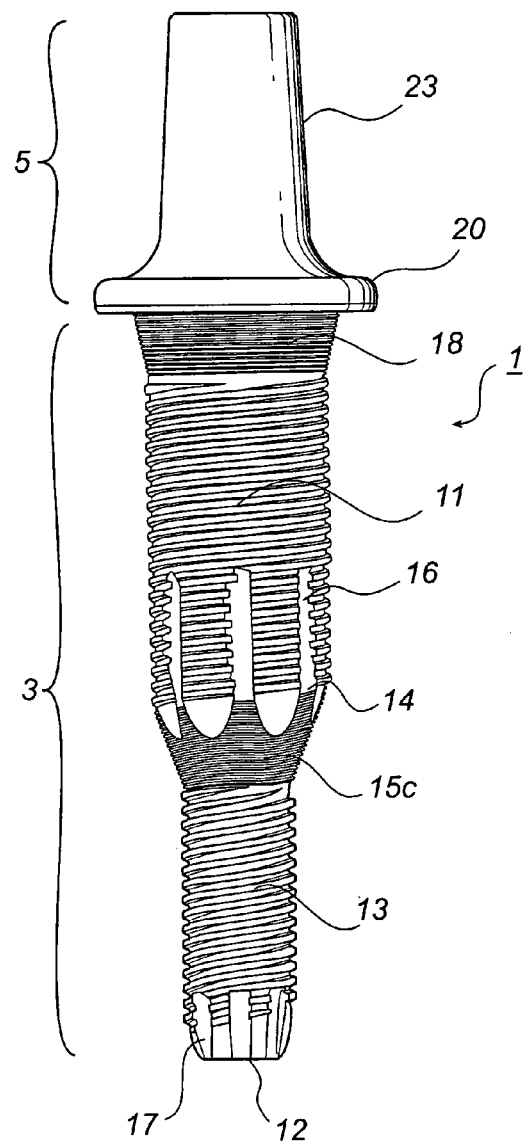
FIG. 11 is a longitudinal side view similar to FIG. 3 of the femur fixture with a connecting section having a screw thread profile.
Figure 12:
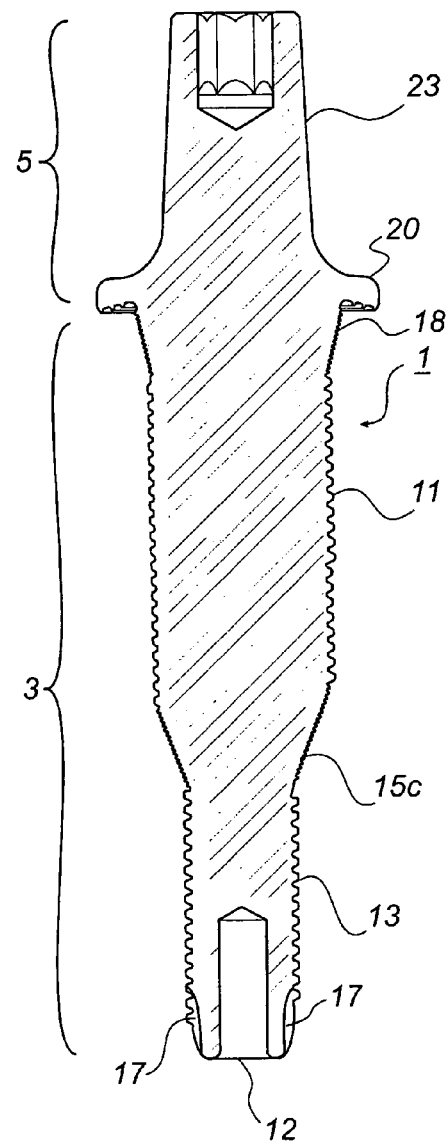
FIG. 12 is a longitudinal sectional view similar to FIG. 4 of the femur fixture with a connecting section having the screw profile.
Figure 13:
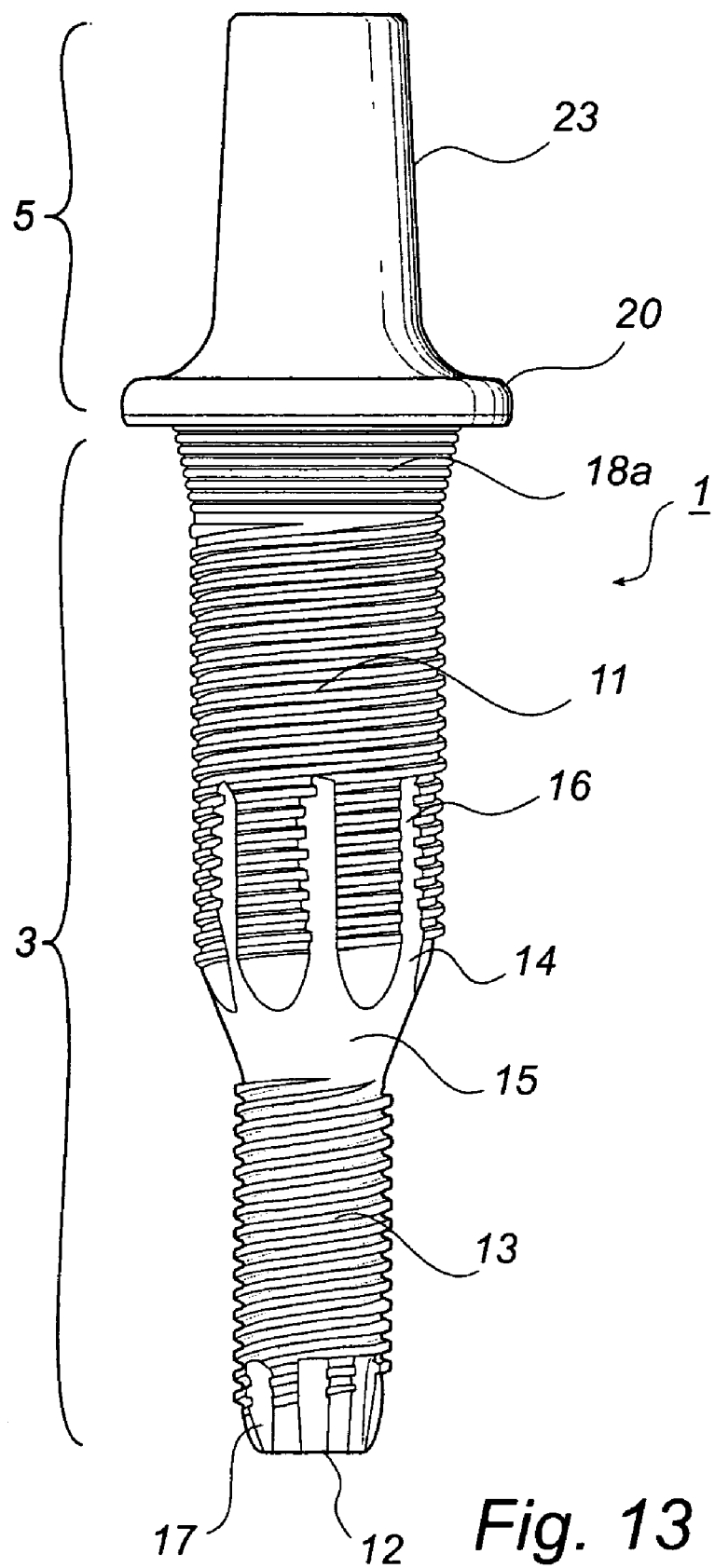
FIG. 13 is a longitudinal side view similar to FIG. 11 of the femur fixture with a connecting section have circumferential beads.
Figure 14:
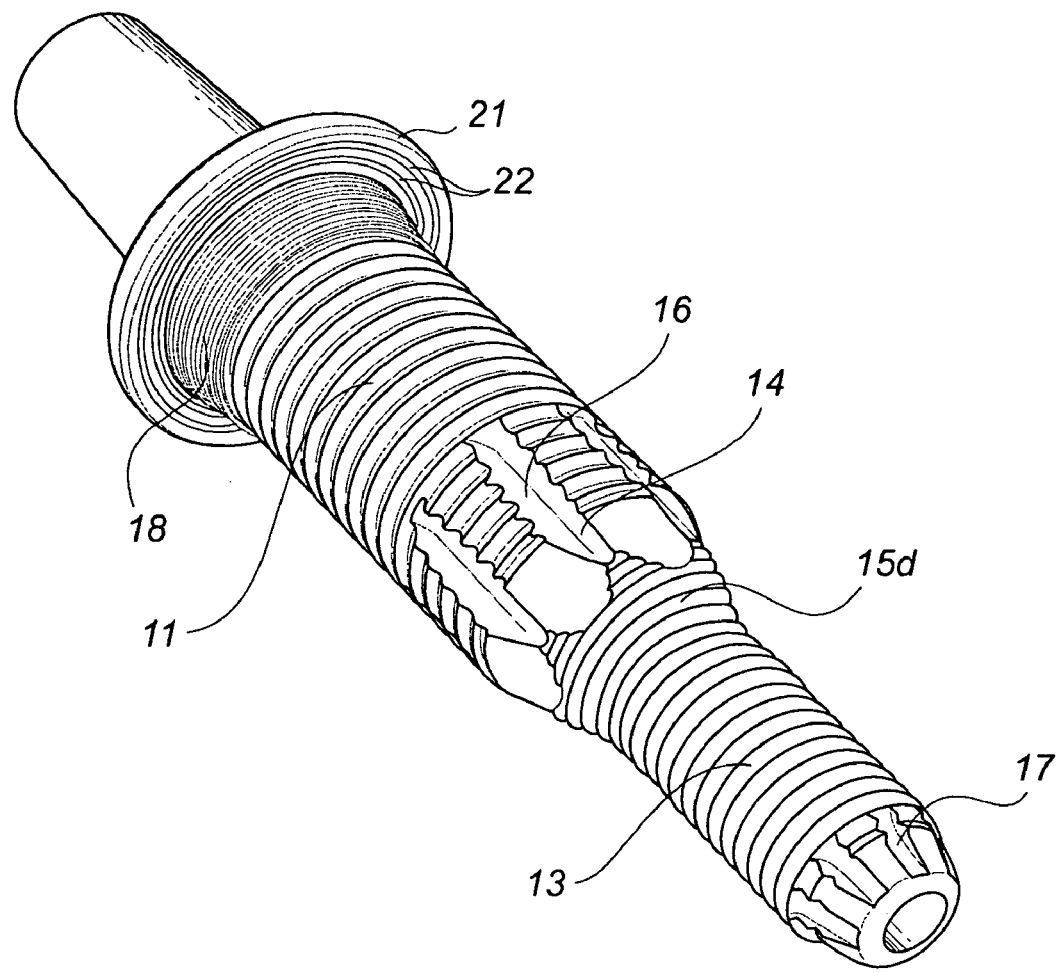
FIG. 14 is a perspective view similar to FIG. 10 of the femur fixture with a connecting section having a screw thread.

In FIGS. 11 and 12, a connecting section 1c is shown having a roughened surface which is at least partly provided with a circumferentially oriented roughness in the shape of a screw thread profile that has a height less than that of the screw thread profiles of the first and second cylindrical sections and no greater than 0.3 mm. FIG. 13 illustrates a proximal section which is provided with a roughness 18a in the form of circumferential beads. In FIG. 14, a connecting section 15d is illustrated having a roughened surface which is at least partly provided with a circumferentially oriented roughness in the shape of a screw thread profile that has a height essentially the same as that of the screw thread profiles of the first and second cylindrical sections.

It will be appreciated that the invention has been described with reference to an exemplary embodiment and that the invention can be varied in many different ways within the scope of the appended claims. For instance, the implant is not confined to use as a femur fixture for a hip-joint prosthesis. As an example, the implant could take the form of a bone fixation screw. It will further be appreciated that the use in the appended claims of reference numerals from the Figures of drawings is for the purposes of illustration and not to be construed as having a limiting effect on the claims.

The invention claimed is:

1. A femur fixture for a hip-joint prosthesis, comprising:
an intraosseous anchoring structure of a generally circular cross-section for screwing laterally into a complementary bore drilled laterally into the neck of a femur after resection of the femur head to an anchored position, the intraosseous anchoring structure being formed from a single, one-piece member and having a proximal end, a distal end, a frusto-conical proximal section at the proximal end, and a proximal cylindrical section having a screw thread profile thereon and extending towards the distal end from the frusto-conical proximal section, the screw thread profile extending from said frusto-conical proximal section towards the distal end, said frusto-conical proximal section being shorter than said proximal cylindrical section, the frusto-conical proximal section and the proximal cylindrical section each being dimensioned so as to bear against the cortex of the femur neck when the intraosseous anchoring structure is in the anchored position; and
a collar section having a distal surface abutting and extending outwardly from the frusto-conical proximal section, said collar section extending generally radially outwardly from the intraosseous anchoring structure,
wherein the intraosseous anchoring structure further has a distal cylindrical section having a screw thread profile thereon and extending towards the proximal cylindrical section from the distal end of the intraosseous anchoring structure, the diameter of said distal cylindrical section being less than the diameter of said proximal cylindrical section.

2. The femur fixture as claimed in claim 1, wherein the intraosseous anchoring structure is so dimensioned that its distal end projects through the lateral cortex of the femur when the intraosseous anchoring structure is in the anchored position.

3. The femur fixture as claimed in claim 1, wherein the screw thread profiles of said proximal and distal cylindrical sections are essentially the same.

4. The femur fixture as claimed in claim 1, wherein said intraosseous anchoring structure further comprises a tapered connecting section provided between and interconnecting said proximal and distal cylindrical sections.

5. The femur fixture as claimed in claim 4, wherein said connecting section has a frusto-conical shape which at one end has a proximal diameter essentially equal to the diameter of said proximal cylindrical section, and at the other end has a distal diameter essentially equal to the diameter of said distal cylindrical section.

6. The femur fixture as claimed in claim 4, wherein said connecting section has a flank angle in the range of 15°–45°.

7. The femur fixture as claimed in claim 4, wherein said connecting section is at least partly provided with a blasted surface.

8. The femur fixture as claimed in claim 4, wherein said connecting section is at least partly provided with a circumferentially oriented roughness.

9. The femur fixture as claimed in claim 8, wherein said circumferentially oriented roughness has a height less than that of the screw thread profiles of said proximal and distal cylindrical sections.

10. The femur fixture as claimed in claim 8, wherein a height of said circumferentially oriented roughness is no greater than 0.3 mm.

11. The femur fixture as claimed in claim 4, wherein said connecting section is at least partly provided with a smooth surface.

12. The femur fixture as claimed in claim 4, wherein the entire surface of said connecting section is smooth.

13. The femur fixture as claimed in claim 4, wherein one or more self-tapping cutting recesses are provided at least in part on said connecting section.

14. The femur fixture as claimed in claim 1, wherein said frusto-conical proximal section at an end thereof interfacing said proximal cylindrical section presents a diameter essentially equal to the diameter of said proximal cylindrical section.

15. The femur fixture as claimed in claim 1, wherein said frusto-conical proximal section has a flank angle in the range of 8–15°.

16. The femur fixture as claimed in claim 1, wherein the frusto-conical proximal section has an axial extent in the range of 5–10 mm.

17. The femur fixture as claimed in claim 1, wherein the frusto-conical proximal section has a proximal diameter in the range of 18–30 mm.

18. The femur fixture as claimed in claim 1, wherein the frusto-conical proximal section is at least partly provided with a roughened surface.

19. The femur fixture as claimed in claim 18, wherein said roughened surface is at least partly a blasted surface.

20. The femur fixture as claimed in claim 18, wherein said roughened surface is at least partly provided with a circumferentially oriented roughness.

21. The femur fixture as claimed in claim 20, wherein said circumferentially oriented roughness is in the shape of a screw thread profile.

22. The femur fixture as claimed in claim 21, wherein the screw thread profile of said frusto-conical proximal section differs from the screw thread profile of said proximal cylindrical section.

23. The femur fixture as claimed in claim 22, wherein the screw thread profile of said frusto-conical proximal section has a height less than the screw thread profile of said proximal cylindrical section.

24. The femur fixture as claimed in claim 21, wherein the height of the screw thread profile on the frusto-conical proximal section is no greater than 0.3 mm.

25. The femur fixture as claimed in claim 21, wherein the screw thread profile on the frusto-conical proximal section is formed by the turns of one or more screw threads.

26. The femur fixture as claimed in claim 20, wherein said circumferentially oriented roughness is in the form of circumferential beads.

27. The femur fixture as claimed in claim 26, wherein said circumferential beads has a height less than that of the screw thread profile of said proximal cylindrical section.

28. The femur fixture as claimed in claim 26, wherein the height of said circumferential beads is no greater than 0.3 mm.

29. The femur fixture as claimed in claim 1, further comprising a head section for supporting a ball component of the hip-joint prosthesis, said head section comprising said collar section.

30. The femur fixture as claimed in claim 29, wherein said distal surface of said collar section is inclined inwardly towards a body of the collar section.

31. The femur fixture as claimed in claim 30, wherein said distal surface of said collar section is inclined inwardly at an inclination angle within the range of 10°–20.

32. The femur fixture as claimed in claim 29, wherein said distal surface of said collar section is concave.

33. The femur fixture as claimed in claim 29, wherein said distal surface of said collar section is provided with radially spaced circular beads.

34. The femur fixture as claimed in claim 33, wherein said circular beads have a height in the range of 0.1–0.5 mm.

35. A set of femur fixtures according to claim 1, wherein the frusto-conical proximal section and the proximal cylindrical section of each fixture in the set have different dimensions, whereby the fixture in the set having the frusto-conical proximal section and the proximal cylindrical section of correct size for abutting the cortex of the femur neck of a particular patient can be selected for use in that patient.

36. A set of femur fixtures according to claim 1, wherein the distal cylindrical sections of all fixtures in the set have the same dimension, and the frusto-conical proximal section and the proximal cylindrical section of each fixture in the set have different dimensions, whereby the fixture in the set having the frusto-conical proximal section and the proximal cylindrical section of correct size for abutting the cortex of the femur neck of a particular patient can be selected for use in that patient.

37. The femur fixture as claimed in claim 1, further comprising a tapered mounting section, said tapered mounting section extending from a proximal end of said collar section to a proximal end of the femur fixture.

* * * * *